(12) United States Patent
Rea

(10) Patent No.: US 11,806,269 B2
(45) Date of Patent: Nov. 7, 2023

(54) OSTOMY BAG VENT SYSTEM FOR USE IN VENTING A GAS FROM AN INTERIOR OF AN OSTOMY COLLECTION POUCH

(71) Applicant: Paul Rea, Rutherford, NJ (US)

(72) Inventor: Paul Rea, Rutherford, NJ (US)

( * ) Notice: Subject to any disclaimer, the term of this patent is extended or adjusted under 35 U.S.C. 154(b) by 107 days.

(21) Appl. No.: 17/203,812

(22) Filed: Mar. 17, 2021

(65) Prior Publication Data
US 2021/0290426 A1    Sep. 23, 2021

Related U.S. Application Data

(60) Provisional application No. 62/990,874, filed on Mar. 17, 2020.

(51) Int. Cl.
*A61F 5/441*    (2006.01)

(52) U.S. Cl.
CPC .................... *A61F 5/441* (2013.01)

(58) Field of Classification Search
CPC .. A61F 5/441; A61F 5/445; A61F 2005/4415; A61F 5/4405
See application file for complete search history.

(56) References Cited

U.S. PATENT DOCUMENTS

| | | | | |
|---|---|---|---|---|
| 5,372,594 A | * | 12/1994 | Colacello | A61F 5/445 604/335 |
| 5,374,254 A | * | 12/1994 | Buma | A61M 25/02 604/533 |
| 2007/0112440 A1 | * | 5/2007 | Perkins | A61F 2/80 623/34 |
| 2010/0010460 A1 | * | 1/2010 | Butler | A61F 5/441 604/333 |

* cited by examiner

*Primary Examiner* — Jessica Arble
*Assistant Examiner* — Timothy L Flynn
(74) *Attorney, Agent, or Firm* — Gearhart Law, LLC

(57) ABSTRACT

A system for use in venting a gas from an interior of an ostomy collection pouch is described. The system is removable and/or reusable in other medical devices. A flange is configured to affix the system to a hole in a wall of the ostomy collection pouch. The flange may have a straight or a curved configuration. In examples, the flange has a 90 degree configuration. Further, the system includes a manual or a passive filter to remove odor from the gas.

20 Claims, 24 Drawing Sheets

OSTOMY BAG VENT SYSTEM FOR USE IN VENTING A GAS FROM AN INTERIOR OF AN OSTOMY COLLECTION POUCH

CROSS-REFERENCE TO RELATED APPLICATION SECTION

This application is a U.S. Non-Provisional Patent Application that claims priority to U.S. Provisional Patent Application No. 62/990,874 filed on Mar. 17, 2020, the entire contents of which are hereby incorporated by reference in their entirety.

FIELD OF THE EMBODIMENTS

The field of the invention and its embodiments relate to a vent system for use in venting a gas from an interior of an ostomy collection pouch. In particular, the present invention and its embodiments provide a removable and reusable vent system for use in venting a gas from an interior of an ostomy collection pouch.

BACKGROUND OF THE EMBODIMENTS

Some diseases, such as bowel cancer, may require the surgical removal of diseased portions of the bowel. The bowel may have to be re-routed through an artificially created hole or opening (e.g., a stoma) in the abdomen so that body waste can still leave the body. The stoma may be permanent (e.g., in the case of bowel cancer or a serious injury) or may be temporary (e.g., while the bowel recover from an infection or inflammation).

An ostomy procedure creates this artificial opening in an organ of the body. Specifically, the artificial opening may be created during a colostomy, an ileostomy, or a gastrostomy. A colostomy is a surgical operation in which a piece of the colon is diverted to the artificial opening in the abdominal wall so as to bypass a damaged part of the colon. An ileostomy a surgical operation in which a piece of the ileum is diverted to the artificial opening in the abdominal wall. A gastrostomy is an opening into the stomach from the abdominal wall, made surgically for the introduction of food.

Current techniques utilize ostomy pouches or bags to collect the body waste. In some examples, the ostomy pouches or bags are made from a plastic film material. A top portion of the ostomy pouch or bag includes a hole with an adhesive substance surrounding the hole. The ostomy pouch or bag is attached to the patient's body over the stoma, such that the body waste can enter the pouch or bag through the opening. A bottom portion of the pouch or bag may include a clamp assembly, whereby the body waste may be removed, while the pouch or bag is still attached to the patient.

However, during use, gases from the body may build up inside of the ostomy pouch or bag and may only be released via the clamp assembly. The gas build up in the interior of the bag or pouch may cause the bag or pouch to become inflated and thus, become bulky and uncomfortable for the patient. This phenomenon is known as "ballooning." To remedy this problem, some ostomy pouches or bags have charcoal filters that function as a deodorizer and allow the gas to escape easily. However, these filters may get blocked with moisture from inside the ostomy pouch or bag. Other solutions use a gaseous vent that may be secured to the pouch at the time of the manufacture or may be inserted through a pre-made opening prior to use by the patient. However, these solutions fail to provide a means by which the vent is removable from the pouch for cleaning. Thus, a need exists for a vent system for use in venting a gas from an interior of an ostomy collection pouch that is removable for cleaning purposes and is reusable in other medical devices. Furthermore, a need exists for a vent system for use in venting a gas from an interior of an ostomy collection pouch that allows/accepts additional accessories to be connected.

Review of Related Technology:

CA 2,142,477 A1 describes an ostomy pouch with a normally-closed vent valve in the form of a slit-providing flexible dome secured to the interior surface of the pouch wall over a vent opening in that wall. An odor-absorbing filter extends across the vent opening (either within the dome or externally of the pouch) to deodorize gases when they are vented from the pouch. The edges of the slit seal against each other to prevent the escape of gases and protect the filter from effluent contact when the dome is in its normal unflexed state but, when the dome is squeezed between the fingers in a prescribed manner, the slit opens to permit the venting of gases from the pouch.

CA 2,246,018 A1 describes a vent for a latex ostomy bag. A flexible patch is mounted over a plurality of small perforations formed in a wall of the bag. The side and bottom edges of the patch are attached adhesively to the surface of the bag so as to form a pouch, with the upper edge of the pouch being free from attachment so as to form an external vent opening. A piece of cotton gauze or other form of porous pad is placed in the pouch, so that accumulated gas in the bag passes into the pouch through the perforations and is vented to the atmosphere via the porous pad.

DE 2,550,766 A1 describes a colostomy container. The container has an inlet aperture and an air removal aperture. The air removal aperture has a hand operated valve that is mounted at a connector position in between colostomy container component constructional sections. The valve may be of the rotary internal constructional type.

EP 156164 B1 describes an air-release valve for medical collecting bags, in particular colostomy bags. The air-release valve has a valve opening and two sealing parts characterized by a base plate with a valve hole and a membrane film, which is made in the form of a flap and is fixed to the base plate and which covers the valve hole, and with a second flap-like film, which is fixed to the base plate opposite the first film and wholly or partially covers the membrane film. The valve regulates the pressure in the bag in such a way that the flaps hold the valve hole sealed up to a positive pressure of about 8 to 20 mm water gauge in the bag.

EP 868892 A1 describes a valve for an ostomy bag. The valve includes a housing attached to the bag and a valve member. The valve member is movable out of predetermined sealing engagement with an interior surface of the housing to open a gas escape path through apertures upon depression of a deformable button portion of the housing. The valve member may comprise a hinged diaphragm, or a centrally mounted plate. The housing may be fitted over a filter element or the filter element may be contained within the housing. The housing could be part of a bagside coupling member, or may include an arrangement for puncturing a hole in the bag when the valve is fitted thereto.

GB 2,094,153 B describes a colostomy appliance. The appliance comprises a stoma bag having a vent outlet provided with a pressure relief valve adapted to open when a predetermined gas pressure is reached in the bag. The vent outlet is associated with a deodorizing filter, through which gas is vented from the bag. The pressure relief valve may comprise a valve housing, at least one inlet port to the housing, at least one outlet port from the housing, a diaphragm valve member sealing the inlet port(s), and a valve seat against which the valve member is urged in fluid-tight contact. The valve member is adapted to lift from the valve seat to open the valve when the valve is subjected to a predetermined fluid pressure.

U.S. Pat. No. 5,372,594 A describes a manual gas vent assembly for use in venting gas from the interior of a conventional unvented ostomy collection pouch. The assembly has an input portion for communicating with the interior of the ostomy collection pouch and an output portion for communicating with the atmosphere. The assembly also includes a mounting device for mounting the valve assembly to a selected portion of the wall of the ostomy collection pouch. The mounting device releasably contains therein a portion of the valve assembly so as to position the input portion thereof proximate the interior of the ostomy collection pouch, and the output portion of the valve assembly proximate to the atmosphere.

U.S. Pat. No. 5,693,035 A describes an ostomy pouch. The pouch is a flexible, shape-recoverable plastic dome that is secured internally to a wall of the pouch over a vent opening. A peripheral portion of the dome spaced from the apex is provided with at least one slit therethrough traversing a radially and axially extending plane of the dome. The slit is curved or arched towards the apex and defines outer and inner lips that normally have their opposing edges in juxtaposition to restrain the escape of gases from the pouch, but permit such escape in quantity when the apical portion of the dome is depressed (by axially squeezing the dome). The lips advantageously have beveled opposing surfaces with the surface of the outer lip generally facing towards the vent opening and that of the inner lip generally facing away from the vent opening. A stop element projects from the apical portion within the dome and is engageable with a deodorizing gas filter located at the base of the dome to limit the extent of deformation of the dome, and to prevent occlusion of the filter by the reverted apical portion of the dome, when the dome is pressed inwardly to open the valve.

U.S. Pat. No. 9,883,964 A describes an ostomy appliance. The appliance comprises an adaptor having a distal end and a proximal end. The distal end is adapted to be coupled to an ostomy wafer and has an opening in fluid communication with an opening in the proximal end. The proximal end is adapted to be coupled to a cap.

Various systems for use in venting a gas from an interior of an ostomy collection pouch are known in the art. However, their structure and means of operation are substantially different from the present disclosure, as the other inventions fail to solve all the problems taught by the present disclosure. The present invention and its embodiments provide a vent system for use in venting a gas from an interior of an ostomy collection pouch. In particular, the present invention and its embodiments provide a removable and reusable vent system for use in venting a gas from an interior of an ostomy collection pouch. Moreover, the present invention and its embodiments provide a removable and reusable vent system that may receive and utilize other attachments, and also provides a filter option.

SUMMARY OF THE EMBODIMENTS

The present invention and its embodiments provide a vent system for use in venting a gas from an interior of an ostomy collection pouch. In particular, the present invention and its embodiments provide a removable and reusable vent system for use in venting a gas from an interior of an ostomy collection pouch.

An embodiment of the instant invention describes a system for use in venting a gas from an interior of an ostomy collection pouch. The system includes numerous components, such as a valve assembly and a flange component. The valve assembly comprises a plunger component, a spring component, a valve body, a first sealing component, and a second sealing component. The flange component is affixed to a hole in a wall of the ostomy collection pouch. The flange component is configured to receive the valve assembly therein such that responsive to a force exerted on a first end of the plunger component, gaseous communication is permitted from an interior to an exterior of the ostomy collection pouch, and upon release of the force exerted on the first end of the plunger component, the gaseous communication is prevented between the interior and the exterior of the ostomy collection pouch.

The plunger component comprises: a first end disposed opposite a second end and a body component disposed between the first end and the second end. The body component comprises one or more protrusions extending from the body component proximate the second end. A width of the body component is smaller than a width of the first end and a width of the second end.

The valve body comprises: a first end disposed opposite a second end and a body component disposed between the first end and the second end. The body component comprises at least one protrusion extending from the body component proximate the second end. The valve body also includes a recessed portion affixed between the second end of the body portion and a ring component.

During assembly, the body component of the plunger component is received by the spring component and the plunger component and the spring component are received by the valve body. The recessed portion is configured to receive the first sealing component. Moreover, the second sealing component is received by the second end of the body portion of the valve body.

Each of the first sealing component and the second sealing component comprise O-rings. A first circumference of the first sealing component is larger than a second circumference of the second sealing component. Further, the first sealing component seals the valve body to the flange component. The second sealing component seals the valve body and seals the plunger component to the valve body.

The flange component may comprise a straight or a curved configuration. Specifically, the flange component comprises: a body component having a first end disposed opposite a second end and a planar portion having a first side disposed opposite a second side. The second end of the body component is affixed to the first side of the planar portion. The flange component comprises an opening disposed therein. The second end of the body component comprises a lip portion. The lip portion of the body component of the flange component is configured to be grasped by a user when utilizing the system.

The first end of the flange component comprises a first opening parallel to the planar portion of the flange component. The first opening is affixed perpendicular to a second opening. In response to the flange component receiving the valve assembly therein, the first opening is configured to receive the at least one protrusion of the body component of the valve body. The valve assembly is rotated such that the at least one protrusion of the body component of the valve body moves from the first opening to the second opening to lock the valve assembly to the flange component.

In some examples, the system may also include a filter affixed on an interior surface of a wall of the ostomy collection pouch over a hole or on the outside of the ostomy collection pouch between the ostomy collection pouch and a flange. The filter may be: a charcoal filter, a hydrophobic filter, or a hydrophilic filter. In other examples, other filter types not explicitly listed may be used with this invention.

One or more components of the system comprise a bio-safe material. In examples, the system and/or parts of the system are removable and/or reusable in another medical device. In other implementations, the system and/or parts of the system are configured for one-time use. In further implementations, parts of the system may be interchanged with other parts.

In general, the present invention succeeds in conferring the following benefits and objectives.

It is an object of the present invention to provide a vent system for use in venting a gas from an interior of an ostomy collection pouch.

It is an object of the present invention to provide a removable vent system for use in venting a gas from an interior of an ostomy collection pouch.

It is an object of the present invention to provide a vent system reusable in other medical devices for use in venting a gas from an interior of an ostomy collection pouch.

It is an object of the present invention to provide a removable and reusable vent system that may receive and utilize other attachments, and also provides a filter option.

DESCRIPTION OF THE PREFERRED EMBODIMENTS

Figure 1:
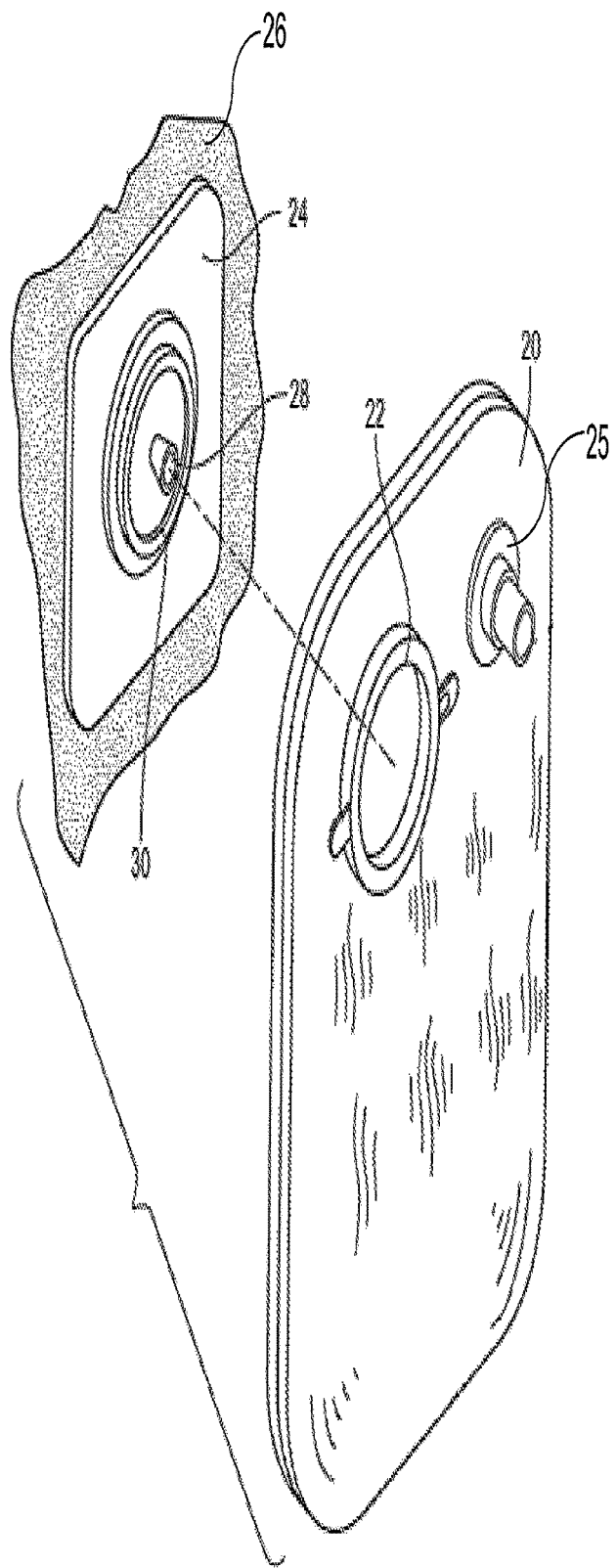
FIG. 1 depicts a perspective view of an ostomy collection pouch affixed to a first embodiment of a flange, according to at least some embodiments described herein.
Figure 2A:
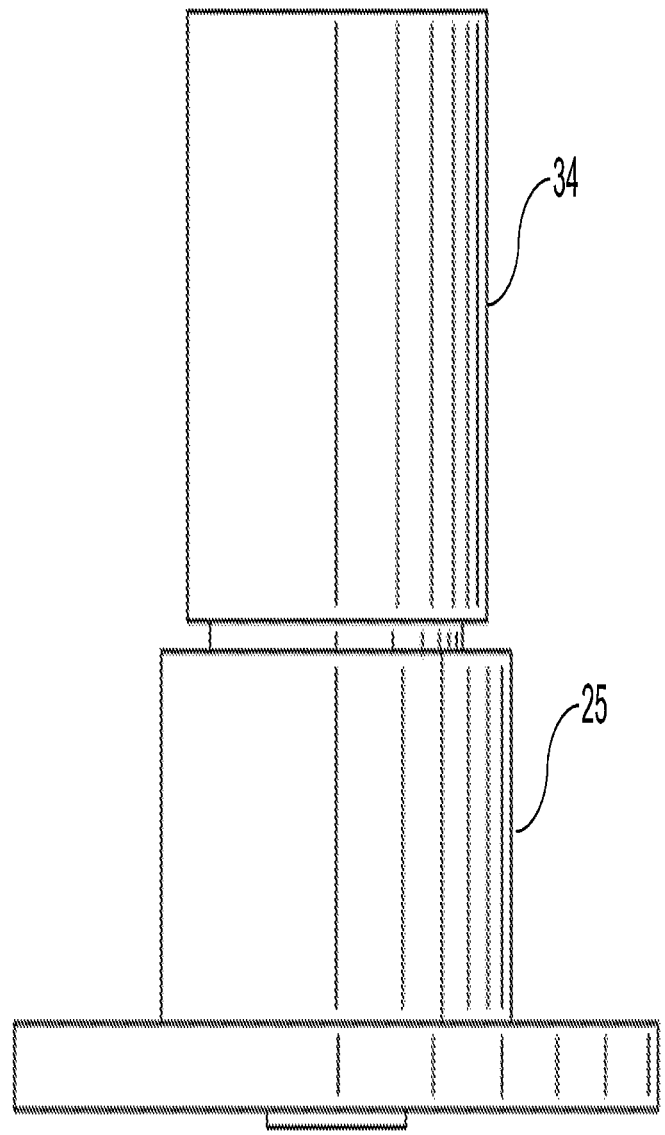
FIG. 2A depicts a side perspective view of a first embodiment of a flange, according to at least some embodiments described herein.
Figure 2B:
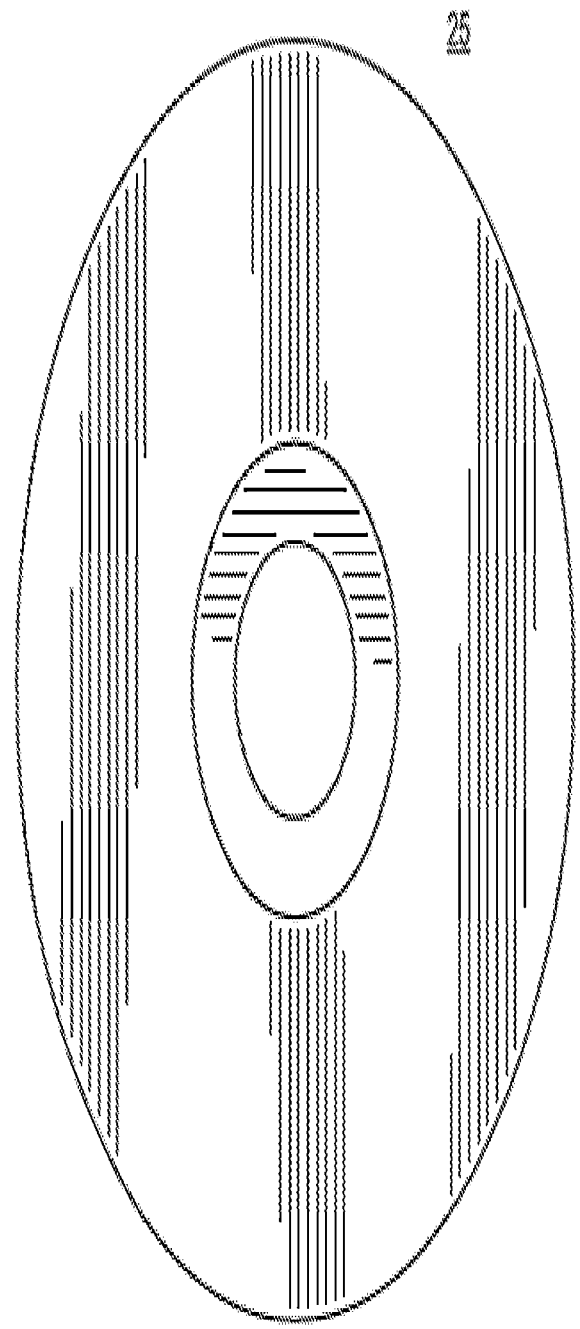
FIG. 2B depicts a bottom perspective view of a first embodiment of a flange, according to at least some embodiments described herein.
Figure 2C:
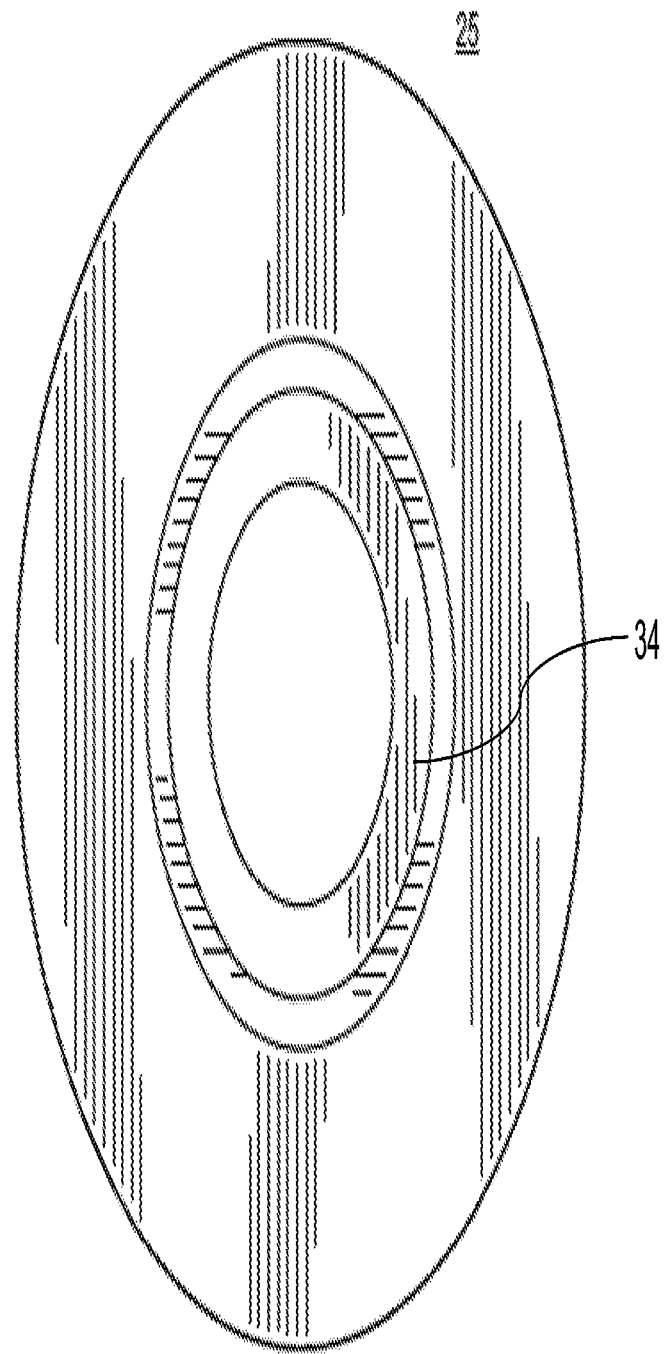
FIG. 2C depicts a top perspective view of a first embodiment of a flange, according to at least some embodiments described herein.
Figure 3A:
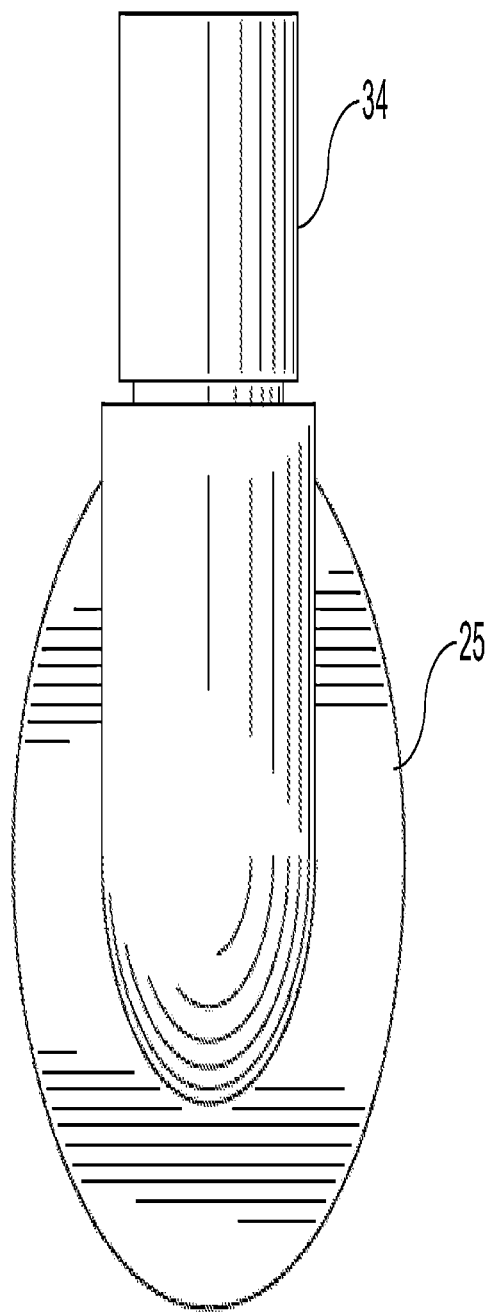
FIG. 3A depicts a front perspective view of a second embodiment of a flange, according to at least some embodiments described herein.
Figure 3B:
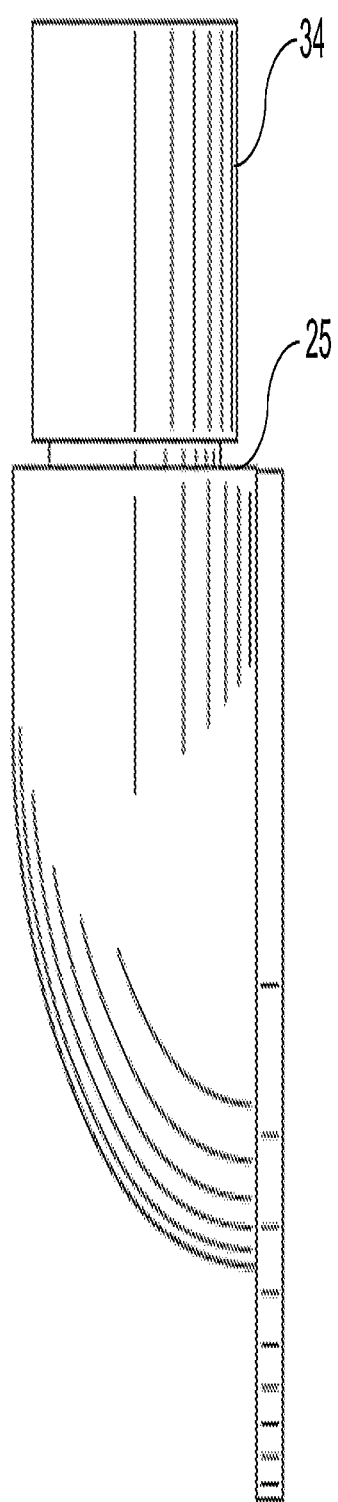
FIG. 3B depicts a side perspective view of a second embodiment of a flange, according to at least some embodiments described herein.
Figure 3C:
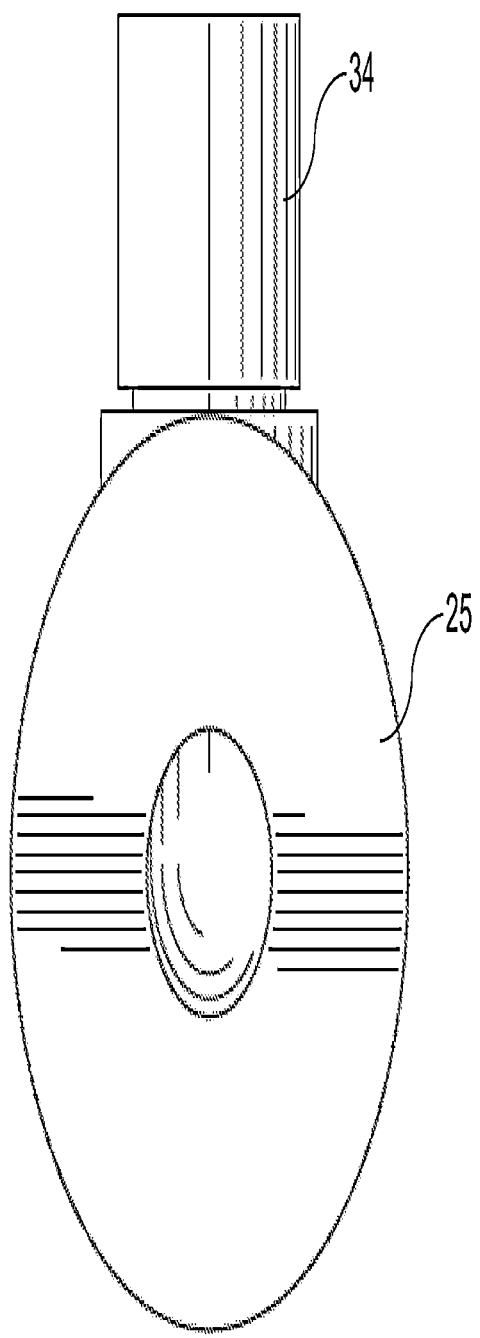
FIG. 3C depicts a back perspective view of a second embodiment of a flange, according to at least some embodiments described herein.
Figure 3D:
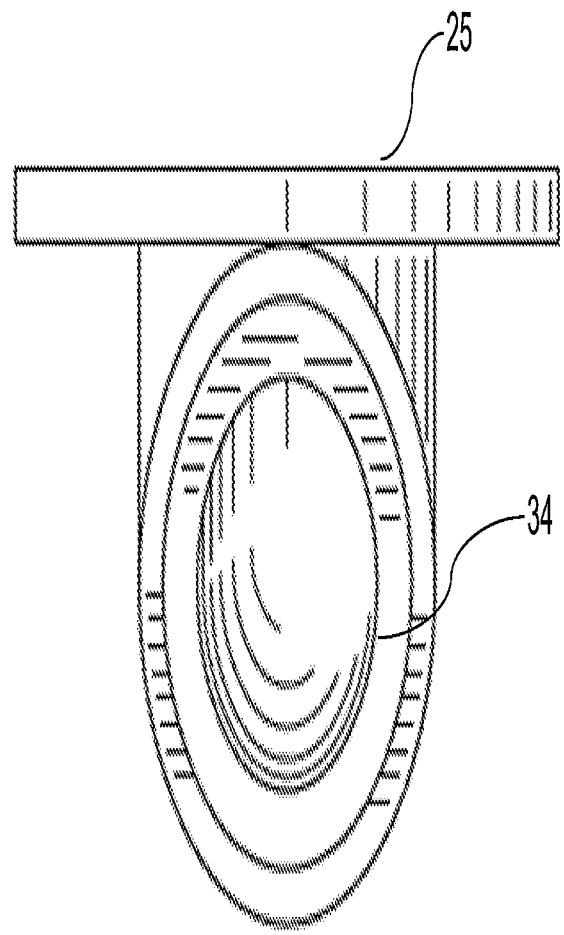
FIG. 3D depicts a top perspective view of a second embodiment of a flange, according to at least some embodiments described herein.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

It should be appreciated that, as described herein, a "stoma" is generally an artificial opening made into a hollow organ, especially one on the surface of the body leading to the gut or trachea. The invention is being described herein in relation to an ostomy procedure, which creates an artificial opening in an organ of the body, and may be created during an operation such as a colostomy, an ileostomy, or a gastrostomy. The description herein is not limited to any one of these operations.

According to FIG. 1, a wafer 24 may be adhesive-backed such that it can be adhered to a skin 26 of a patient. In other examples, an adhesive may be added or applied to an ostomy collection pouch 20. The ostomy collection pouch 20 is disposable or reusable. In examples, the ostomy collection pouch 20 is a flexible and shape-recoverable pouch that may comprise a plastic material. The adhesive may be a medical grade adhesive material or composition of a homogenous blend of one or more materials. In some examples, the adhesive may comprise one or more natural or synthetic polymers. In this case, the wafer 24 may be adhered to the skin 26 of the patient such that a stoma 28 of the patient is surrounded by an opening provided by the wafer 24. As such, the wafer 24 provides a first mount 30. As explained supra, the stoma 28 may be permanent or temporary, based on the underlying disease or condition. An ostomy procedure creates this artificial opening in an organ of the body. Specifically, the artificial opening may be created during a colostomy, an ileostomy, or a gastrostomy.

The first mount 30 is adapted to cooperate with a second mount 22 disposed on the ostomy collection pouch 20. Moreover, a first embodiment of a flange 25 may be affixed to the ostomy collection pouch 20, as depicted in FIG. 1. In examples, the flange 25 may be affixed to the ostomy collection pouch 20 via a water-tight adhesive. In other examples, the flange 25 may be molded into the ostomy collection pouch 20 when the ostomy collection pouch 20 is manufactured. In additional examples, the flange 25 may be mechanically connected to the ostomy collection pouch 20 in any number of ways, such as via compression fitting.

As shown in FIG. 1, FIG. 2A-FIG. 2C, the first embodiment of the flange 25 is of a straight configuration. As shown in FIG. 3A-FIG. 3D and FIG. 4-FIG. 19, the second embodiment of the flange 25 is of a curved configuration. In some examples, the second embodiment of the flange 25 has a 90 degree configuration. However, it should be appreciated that other angles are contemplated for the second embodiment of the flange 25.

Figure 4:
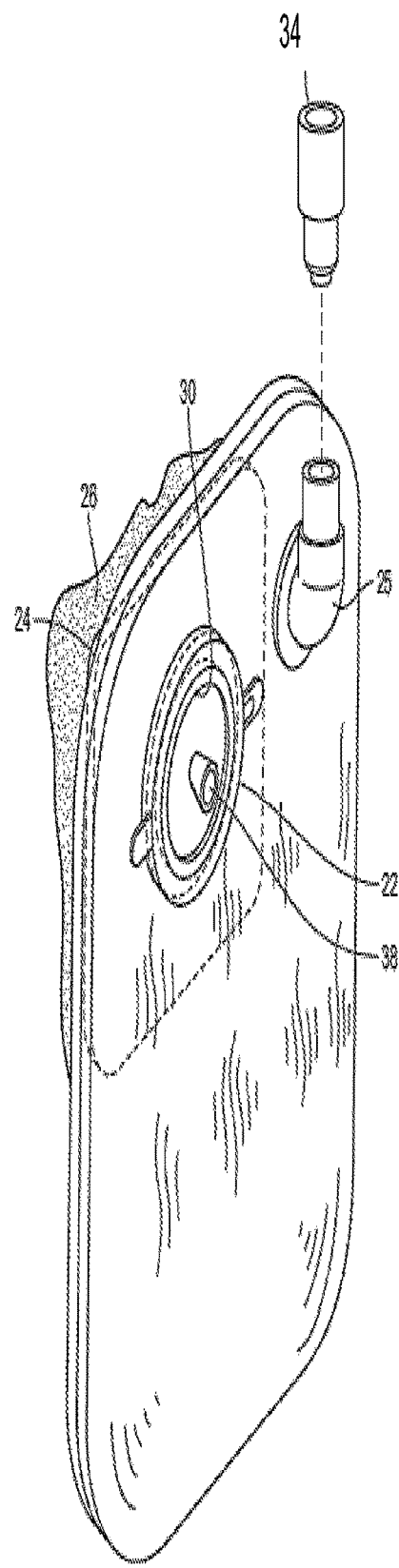
FIG. 4 depicts a perspective view of an installed ostomy collection pouch affixed to a second embodiment of a flange, the second embodiment of the flange being configured to receive a valve body, according to at least some embodiments described herein.

As shown in FIG. 4, there is a first mount 30 and a second mount 22 that allows for the stoma 38 to be secured to the ostomy collection pouch 20. A valve body 34 is received by the first embodiment or the second embodiment of the flange 25 such that the valve body 34 may be mounted on the ostomy collection pouch 20. In some examples, the valve body 34 may be friction fit into either the first embodiment or the second embodiment of the flange 25. In other examples, the valve body 34 may be connected to either the first embodiment or the second embodiment of the flange 25 via a threaded connection. In further examples, the valve body 34 may be connected to either the first embodiment or the second embodiment of the flange 25 via some other connection method not explicitly listed herein, such as a Bayonet method.

It should be appreciated that the valve body 34 may be removable from the first embodiment or the second embodiment of the flange 25 (e.g., for cleaning purposes) and/or are reusable in another medical device and/or are interchangeable with other components or accessories. The devices for which the valve body 34 may be used in is non-exhaustive and numerous devices are contemplated herein. Moreover, it should be appreciated that the uses for the flange 25 are non-exhaustive and are provided for illustrative purposes only.

Figure 5:
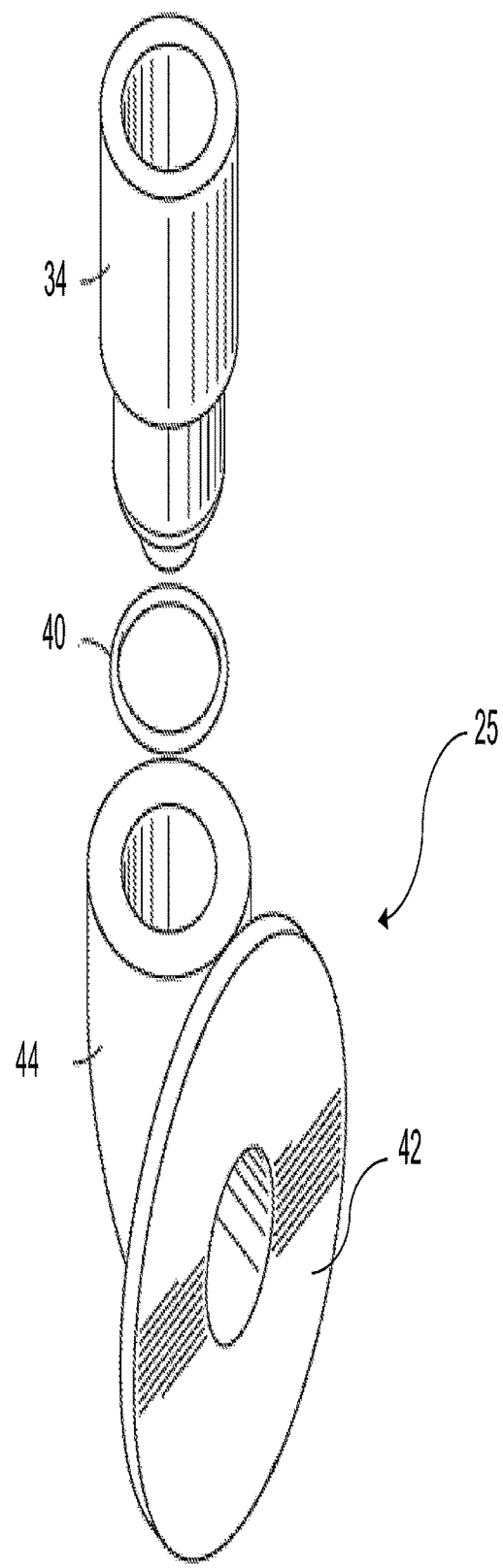
FIG. 5 depicts an exploded view of a second embodiment of a flange configured to receive a valve body, according to at least some embodiments described herein.

Specifically, the first embodiment or the second embodiment of the flange 25 affixes the valve body 34 to a hole in a wall of the ostomy collection pouch 20 to allow air to pass from the ostomy collection pouch 20 and out through the first embodiment or the second embodiment of the flange 25. During use of the ostomy collection pouch 20, gases from the body may build up inside of the ostomy collection pouch 20, forcing the ostomy collection pouch 20 to become inflamed, bulky and uncomfortable for the patient. The system described herein is used to relieve this gaseous pressure. As shown in FIG. 5, the valve body 34 and a sealing component 40 may be affixed to a body 44 of the second embodiment of the flange 25.

Figure 7:
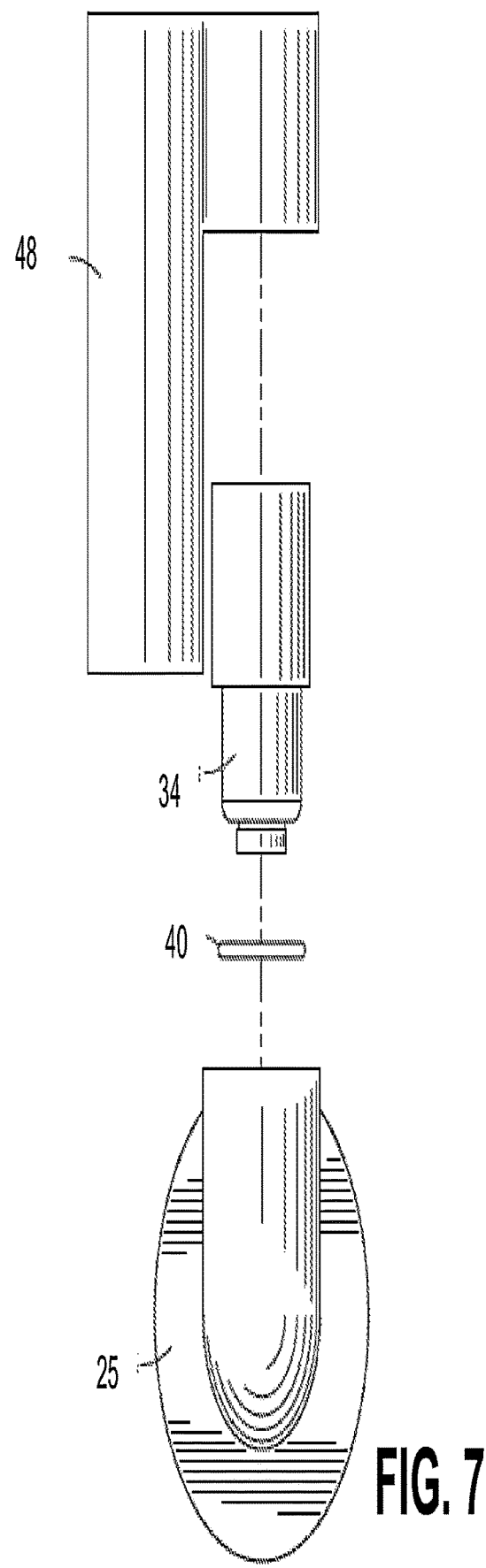
FIG. 7 depicts an exploded view of a second embodiment of a flange, a valve body, and a manual filter, according to at least some embodiments described herein.
Figure 8:
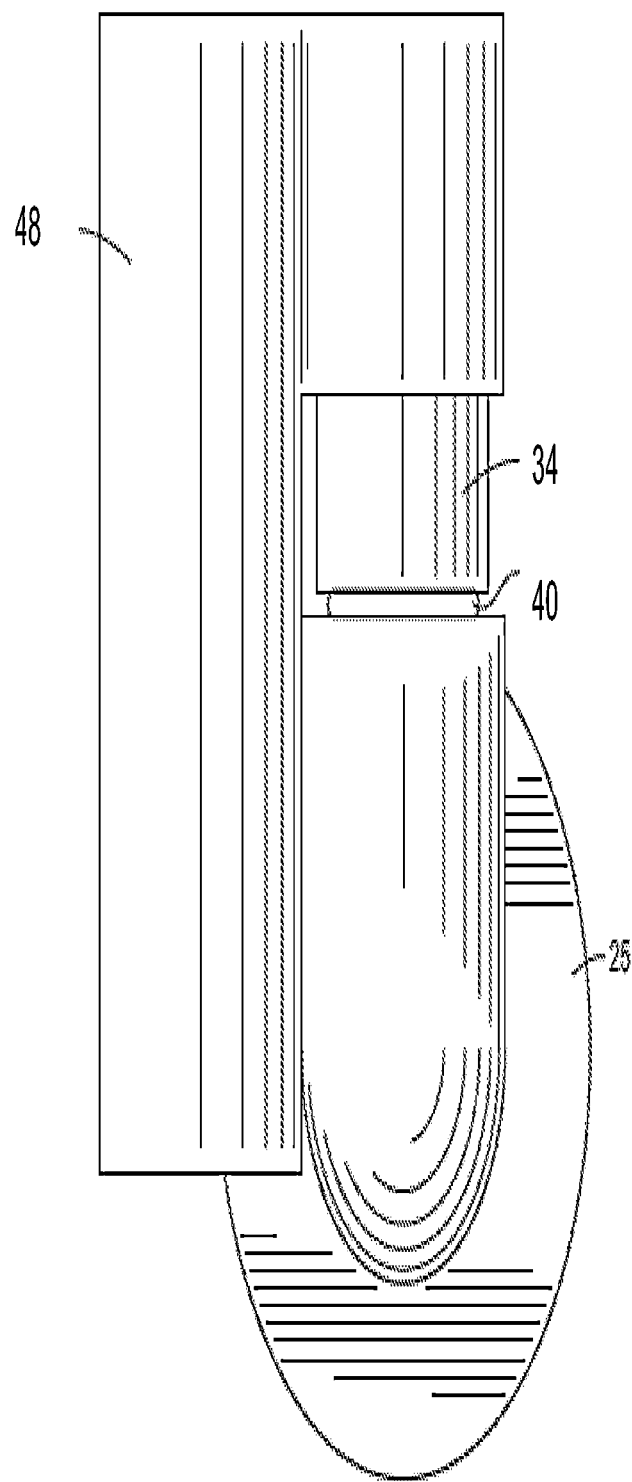
FIG. 8 depicts a front perspective view of a valve body having a filter component, according to at least some embodiments described herein.
Figure 9:
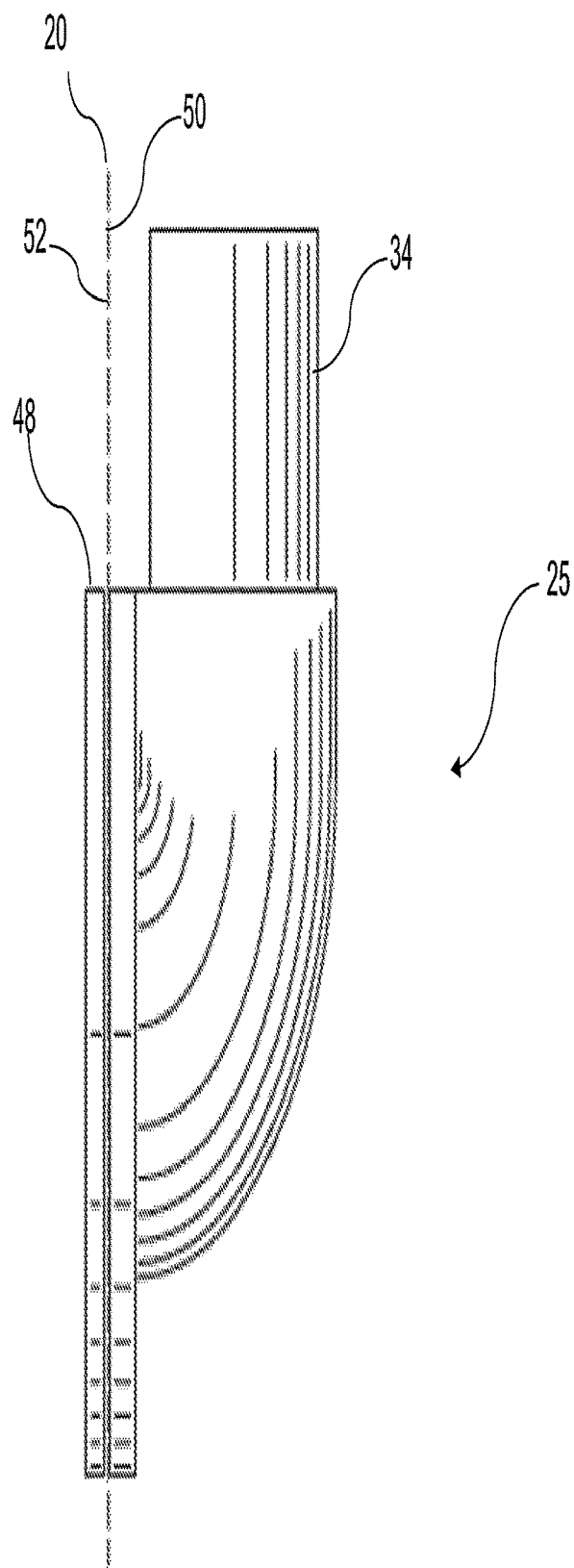
FIG. 9 depicts an alternative filter component adhered to an interior surface of an ostomy collection pouch, according to at least some embodiments described herein.
Figure 10:
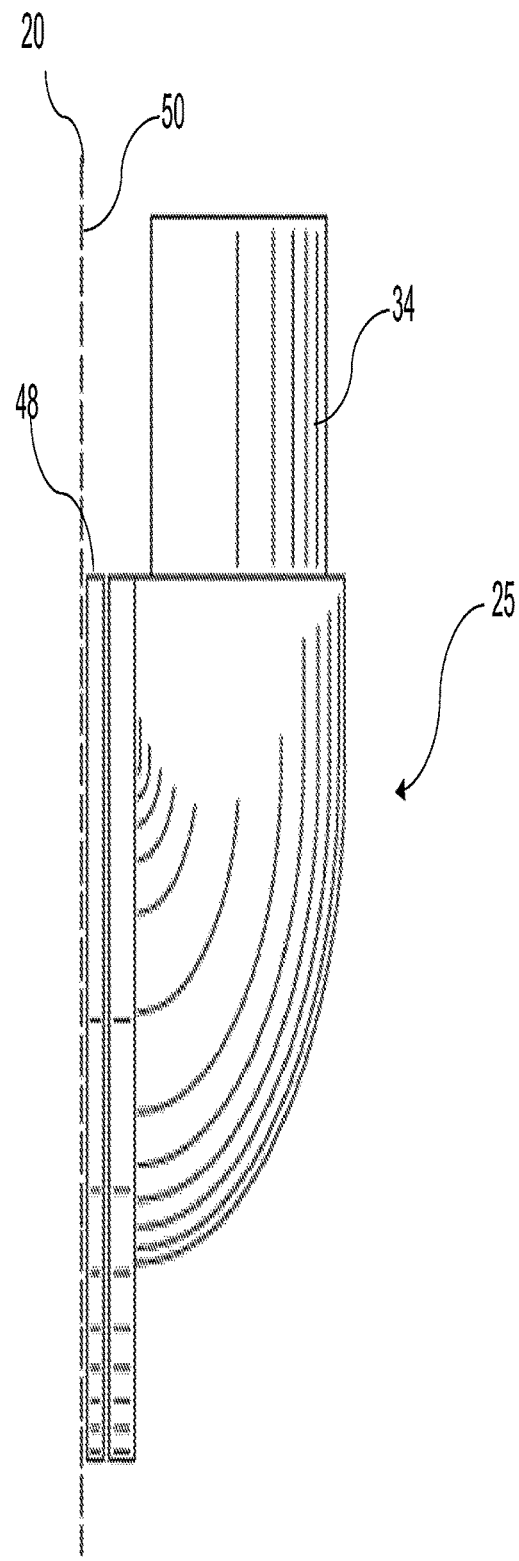
FIG. 10 depicts an alternative filter component adhered to an exterior surface of an ostomy collection pouch, according to at least some embodiments described herein.
Figure 11:
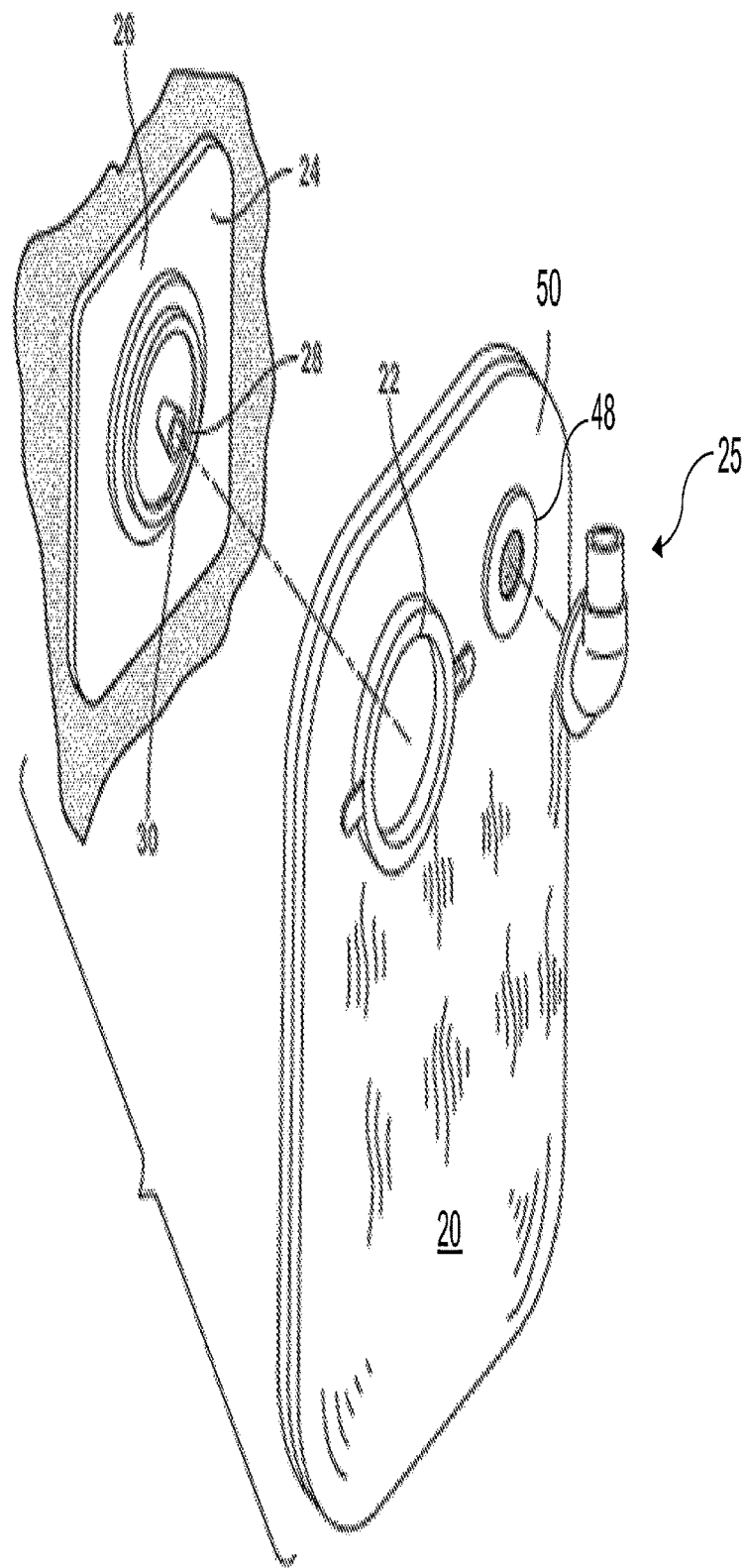
FIG. 11 depicts a perspective view of an alternative filter component affixed to an exterior surface of an ostomy collection pouch, according to at least some embodiments described herein.
Figure 12:
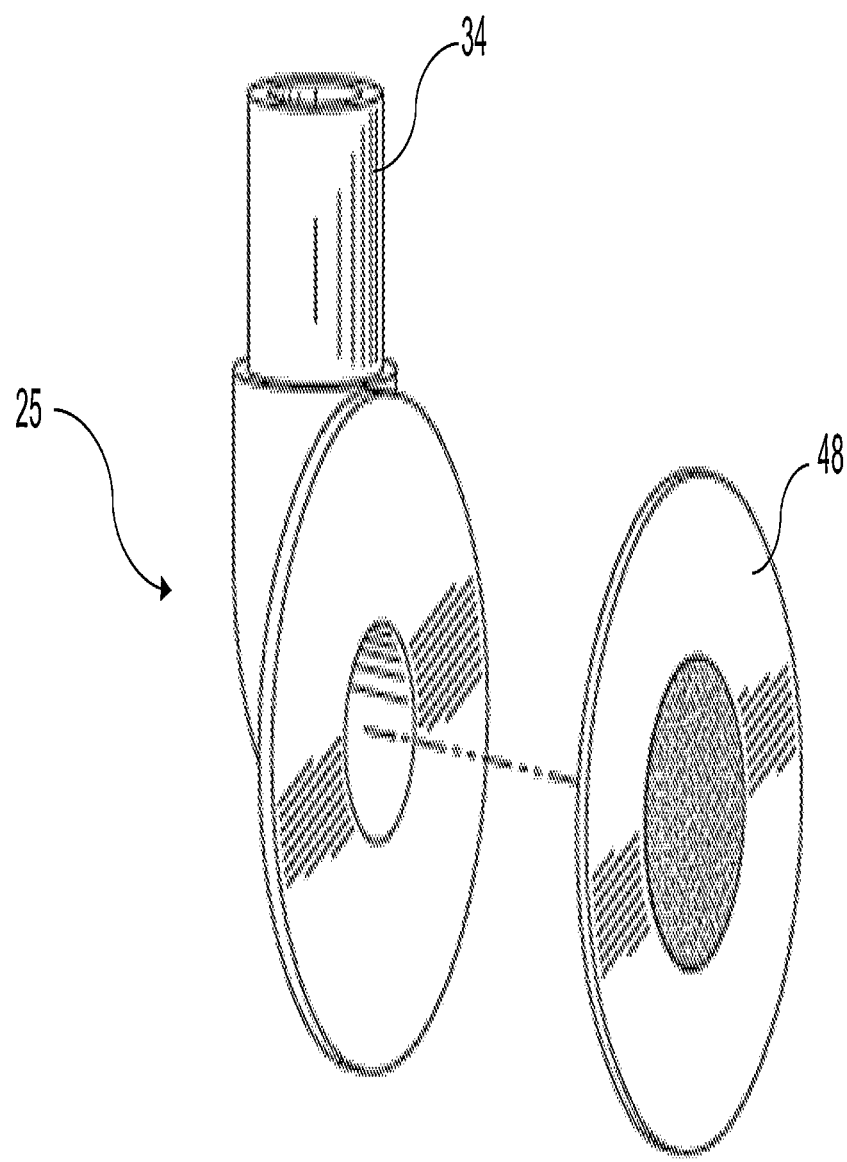
FIG. 12 depicts a rear perspective view of an alternative filter component behind a second embodiment of a flange, according to at least some embodiments described herein.
Figure 13:
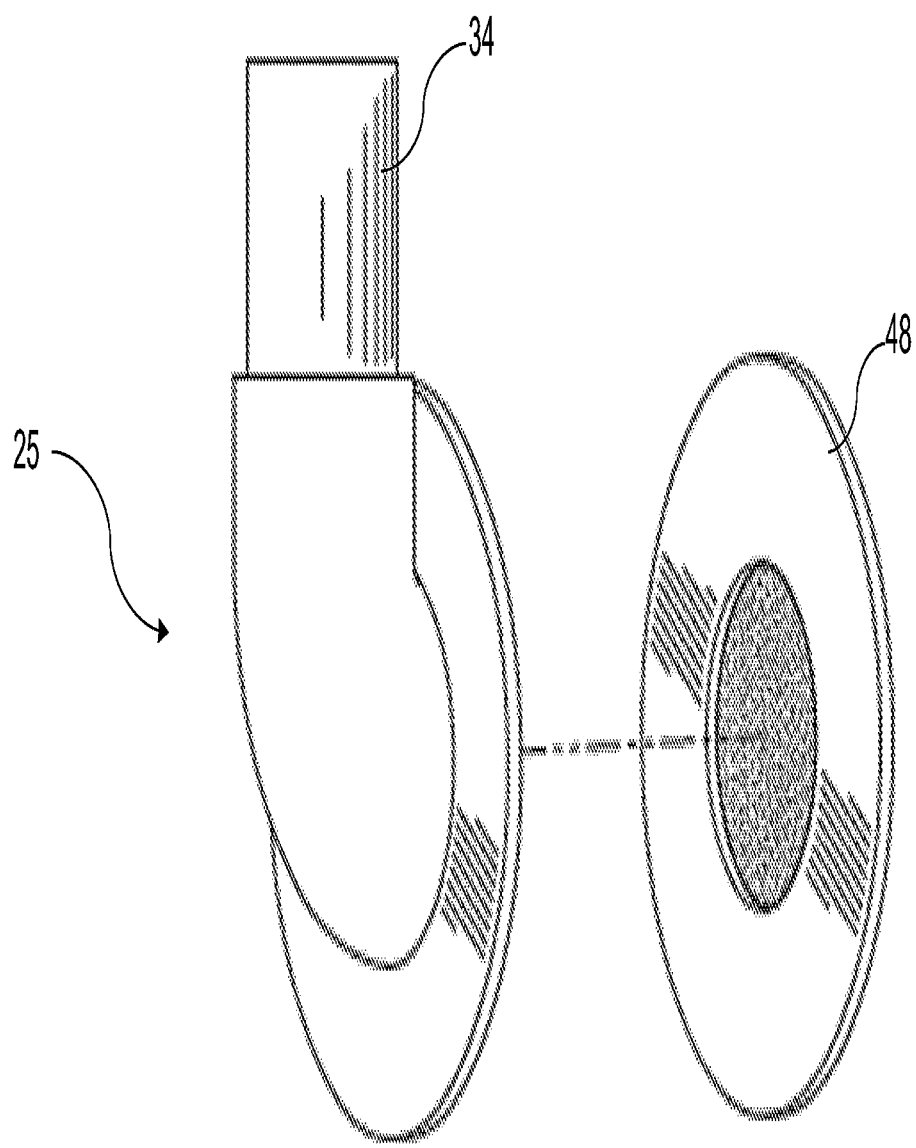
FIG. 13 depicts a front perspective view of an alternative filter component behind a second embodiment of a flange, according to at least some embodiments described herein.

As shown in FIG. 6, FIG. 7, FIG. 8, FIG. 9, and FIG. 10, the system described herein may optionally utilize a filter 48. The filter 48 connects to the first or the second embodiment of the flange 25 via friction fit, a threaded fit, or some other connection means. In FIG. 9, an alternative filter component (e.g., the filter 48) is adhered to an interior surface 52 of the ostomy collection pouch 20. In this example, the alternative filter component may be used with the second embodiment of the flange 25. FIG. 9 also depicts an exterior surface 50 of the ostomy collection pouch 20. In FIG. 10, another alternative filter component (e.g., the filter 48) is adhered to an exterior surface 50 of the ostomy collection pouch 20 between the ostomy collection pouch 20 and the second embodiment of the flange 25. FIG. 11 also depicts a further alternative filter component (e.g., the filter 48) affixed to the exterior surface 31 of the ostomy collection pouch 20. This further alternative filter component (e.g., the filter 48) is also depicted in FIG. 12 (as a rear view) and in FIG. 13 (as a front view) and may be used in conjunction with the second embodiment of the flange 25.

The filter 48 described herein may be a charcoal filter, a hydrophobic filter, and/or a hydrophilic filter. It should be appreciated that other filtering methods not explicitly listed herein may be used as well. The filter 48 may be configured deodorize the gas and/or remove moisture from the gas. In additional examples, an absorbent material or a superabsorbent material may cover the filter 48 to remove the moisture from the gas prior to the gas passing through the filter 48, and thus, preventing blockage of the filter 48, the flange 25 and/or the valve assembly 34.

In some examples, the filter 48 is a manual filter (as depicted in FIG. 7 and FIG. 8). Released air is taken into the filter 48, where odor from the air is absorbed, and odor-less air flows out of the filter 48. It should be appreciated that a length of the exiting filter stem of the filter 48 may be adjusted to add more or less filter material.

Figure 6:
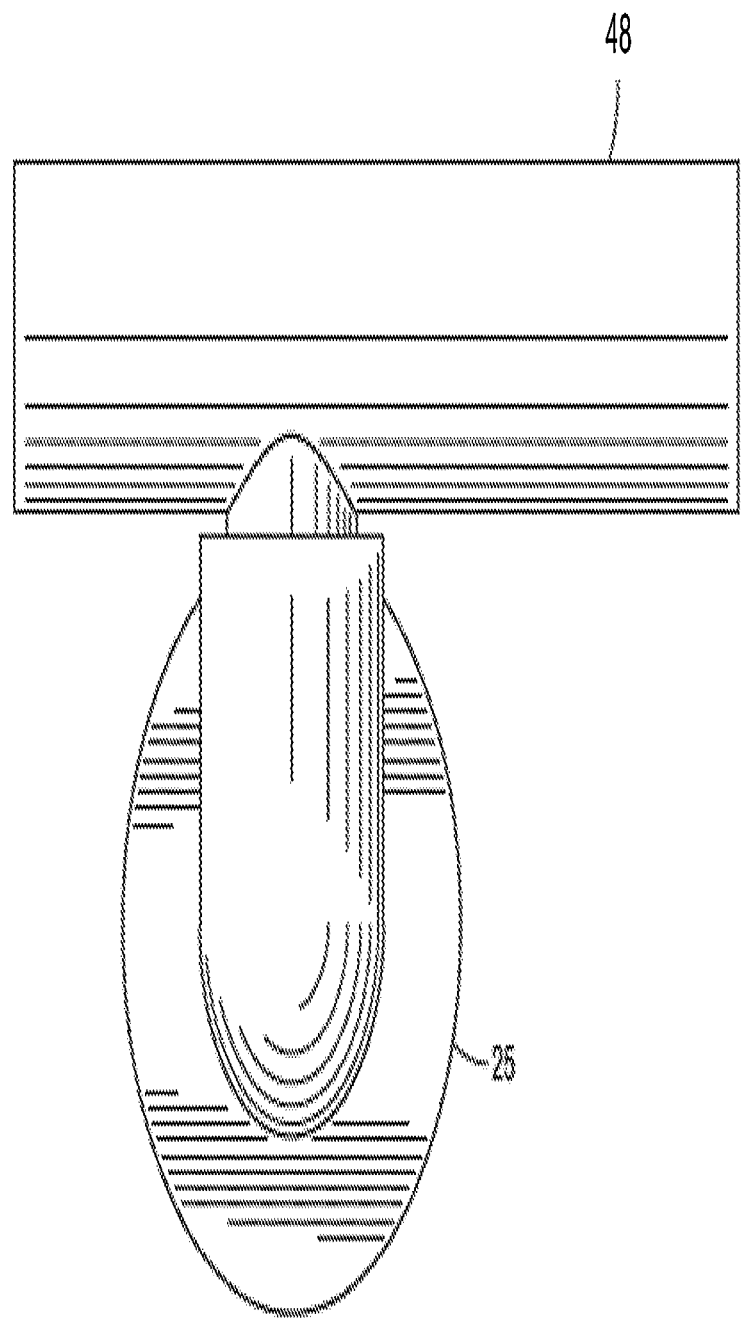
FIG. 6 depicts a perspective view of a passive filter affixed to a second embodiment of a flange, according to at least some embodiments described herein.

In other examples, the filter is a passive filter (as depicted in FIG. 6). In this scenario, the passive filter (e.g., the filter 48) may be connected to the first or the second embodiment of the flange 25 via a threaded connection or a friction fit connection. In this example, the passive filter may be used overnight or for any use case where the user does not wish to manually evacuate gas from the ostomy collection pouch 20 via the system.

In some examples, the passive filter 48 may include one or more chambers. In some examples, the filter 48 may have a front chamber and a rear chamber. The rear chamber may have a stem with an opening that can be inserted into the flange 25. The front chamber may contain the filter 48 and another opening to the outside air. A partition may separate the front chamber and the rear chamber. In some examples, one or more holes may be present at the top of the partition to allow air to pass between the front chamber and the rear chamber. In specific examples, two holes may be present at the top of the partition to allow air to pass between the front chamber and the rear chamber. Any liquid, stoma output, and/or stool material that passes the flange 25 and enters the rear chamber may be contained in the rear chamber, such that it does not reach the holes at the top of the partition. The liquid, stoma output, and/or stool material may then drain back through the flange 25.

Figure 14:
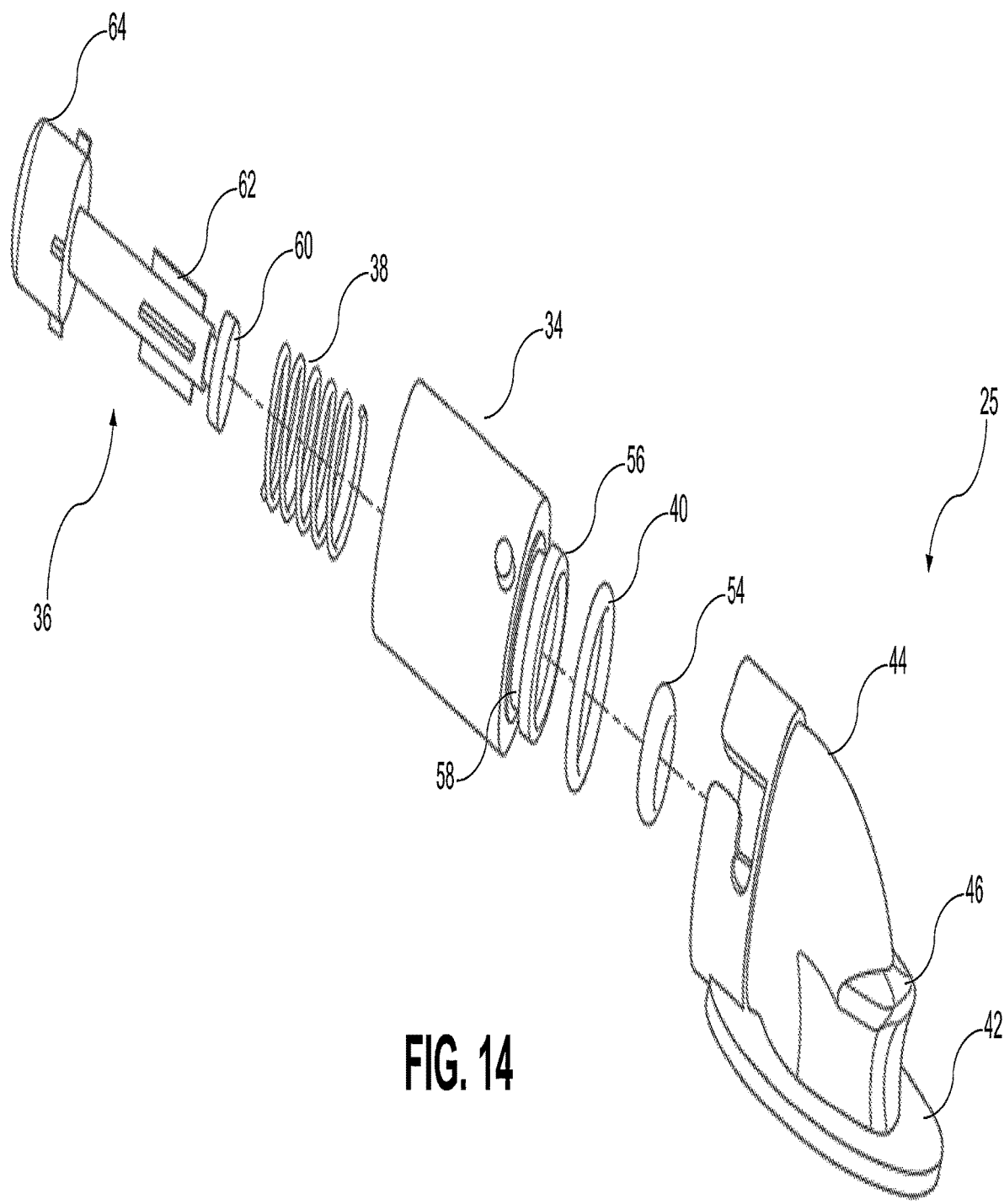
FIG. 14 depicts an exploded view of a system, according to at least some embodiments described herein.

As shown in FIG. 14, a system for use in venting a gas from an interior of an ostomy collection pouch 20 is described and depicted. The system includes numerous components, such as a valve assembly and a flange component (e.g., the first or the second embodiment of the flange 25). The valve assembly comprises: a plunger component 36, a spring component 38, a valve body 34, a first sealing component 40, and a second sealing component 54. The valve assembly is received by the flange 25. In some examples, the valve assembly is screwed into the flange 25.

The plunger component 36 includes a first end 64 disposed opposite a second end 60 and a body component disposed between the first end 64 and the second end 60. The body component of the plunger component 36 comprises one or more protrusions (or fins or wings) 62 extending from the body component proximate the second end 60. In preferred examples, a quantity of the one or more protrusions (or fins or wings) 62 extending from the body component proximate the second end 60 is four, but other quantities are contemplated by Applicant.

It should be appreciated that other designs for the one or more protrusions 62 may be used besides the designs explicitly listed herein. For example, some designs may include larger wings or a larger rod with air channels built into the rod design, among others. The one or more protrusions 62 function as stabilizers that maintain the plunger component 36 in the center of the valve body 34, and also provide a channel for gas to pass by the plunger component 36.

A width of the body component of the plunger component 36 is smaller than a width of the first end 64 and a width of the second end 60. In other examples, the width of the body component of the plunger component 36 is identical to the width of the first end 64 and the of the second end 60, where different air channels are added, as well as a place for the second sealing component 54 to sit on the plunger component 36.

The valve body 34 comprises a first end disposed opposite a second end and a body component disposed between the first end and the second end. The body component of the valve body 34 comprises at least one protrusion 72 (of FIG. 15, FIG. 16, and FIG. 17) extending from the body component proximate the second end. The valve body 34 also includes a recessed portion 58 affixed between the second end of the body portion and a ring component 56.

Figure 15:
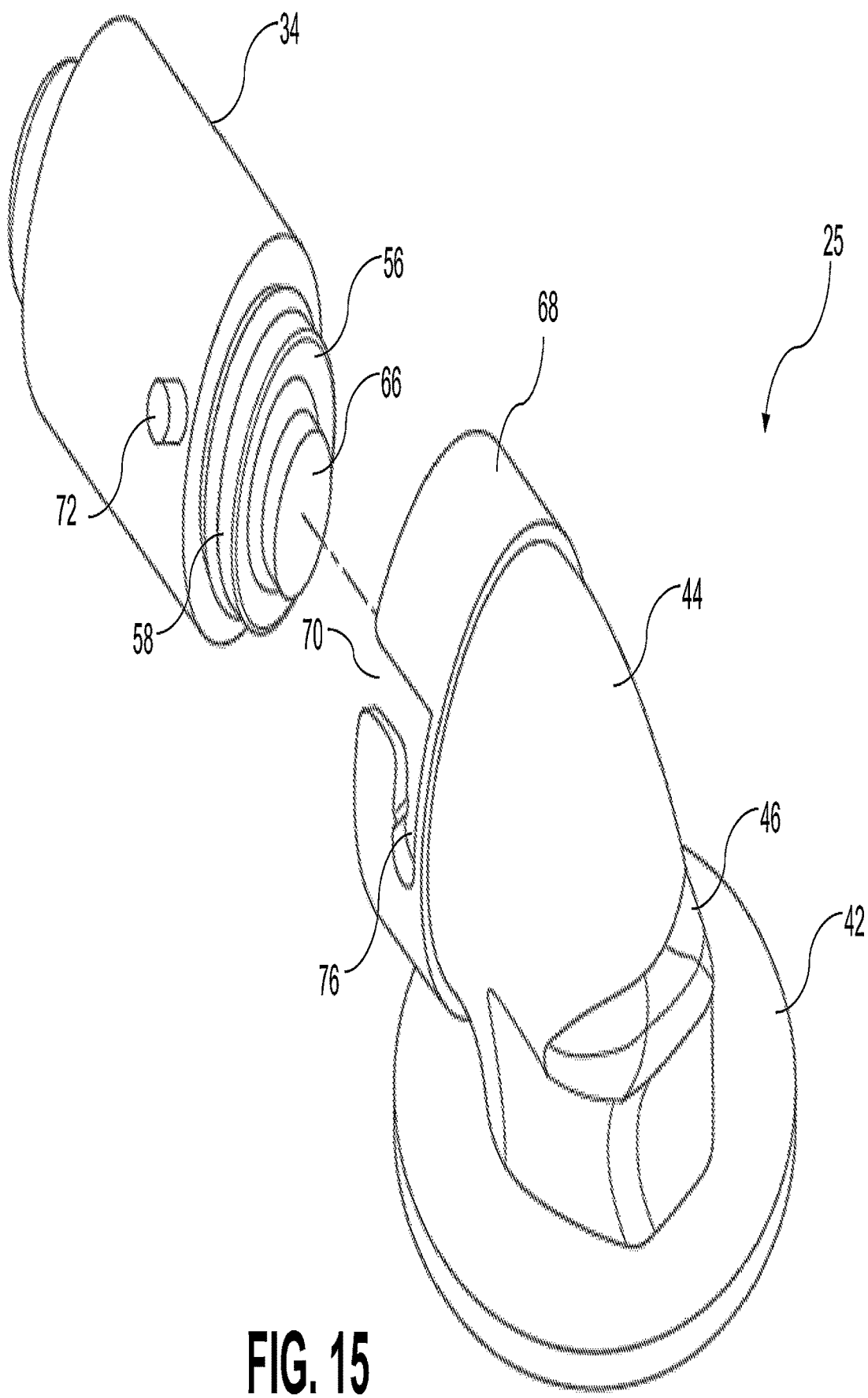
FIG. 15 depicts a front perspective view of a valve body and a second embodiment of a flange, according to at least some embodiments described herein.
Figure 16:
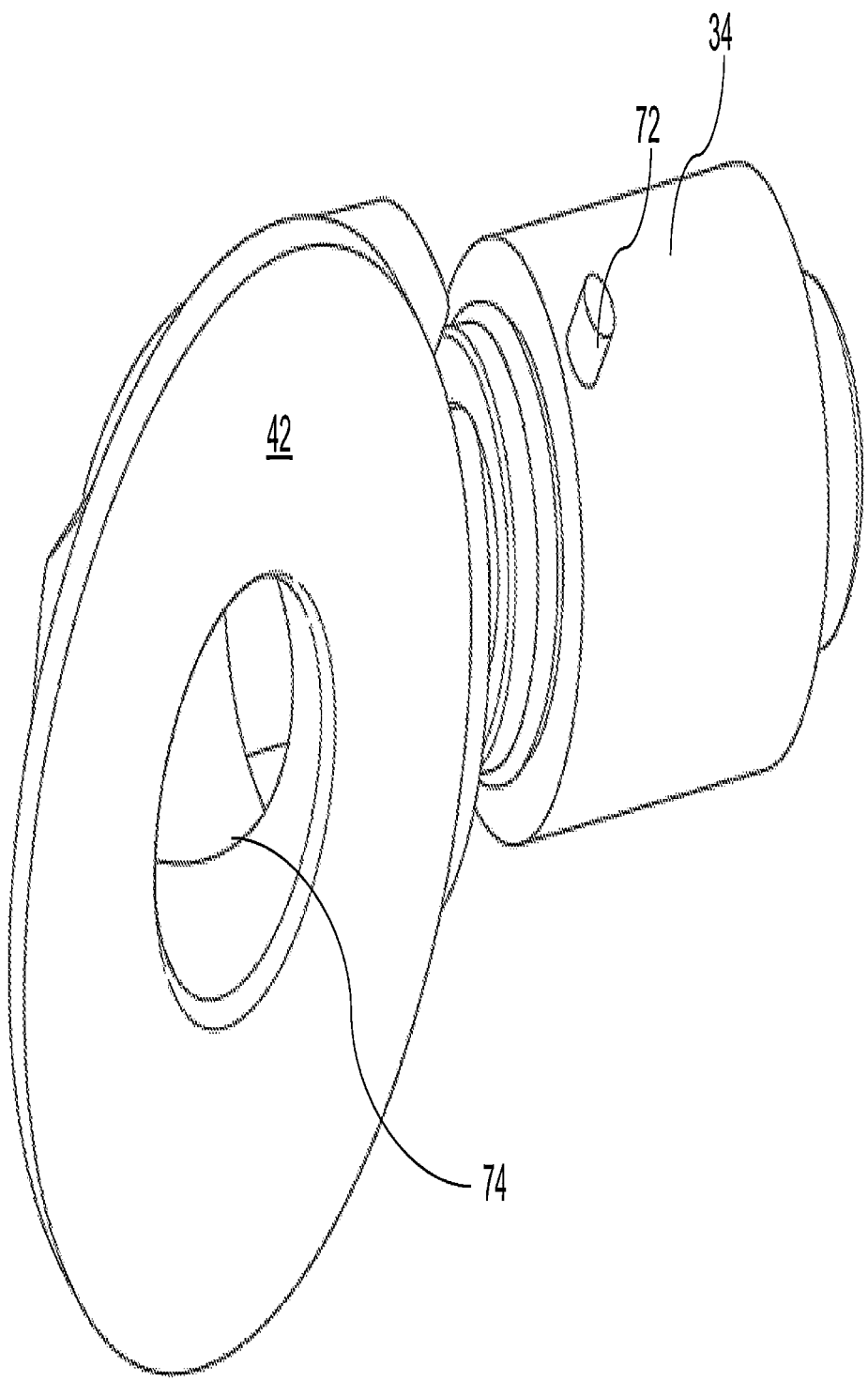
FIG. 16 depicts a rear perspective view of a valve body and a second embodiment of a flange, according to at least some embodiments described herein.

Moreover, in examples, and as shown in FIG. 15 and FIG. 16, the valve body 34 is configured with a Bayonet style valve body. It should be appreciated that the Bayonet style valve body is a press fit or "twist lock" style.

Each of the first sealing component 40 and the second sealing component 54 comprise O-rings. A first circumference of the first sealing component 40 is larger than a second circumference of the second sealing component 54.

To assemble the valve assembly, the body component of the plunger component 36 is received by the spring component 38. The plunger component 36 and the spring component 38 are received by the valve body 34. Moreover, the recessed portion 58 of the valve body 34 is configured to receive the first sealing component 40. The second sealing component 54 is received by the second end of the body portion of the valve body 34. It should be appreciated that the one or more protrusions (or fins or wings) 62 serve to keep the body component of the plunger component 36 centered in the valve body 34.

Moreover, when assembled and in some examples, the first end 64 of the plunger component 36 may be a flat surface that may be flush or recessed with the first end of the valve body 34. In other examples, when assembled, the first end 64 of the plunger component 36 comprises a push body component that protrudes from the first end of the valve body 34, making it easier for the user to engage with the assembly. Further, when the valve assembly is assembled, the first sealing component 40 seals the finished valve assembly to the flange component 42. Further, the second sealing component 54 seals the valve body 34 and seals the plunger component 36 to the valve body 34.

Figure 19:
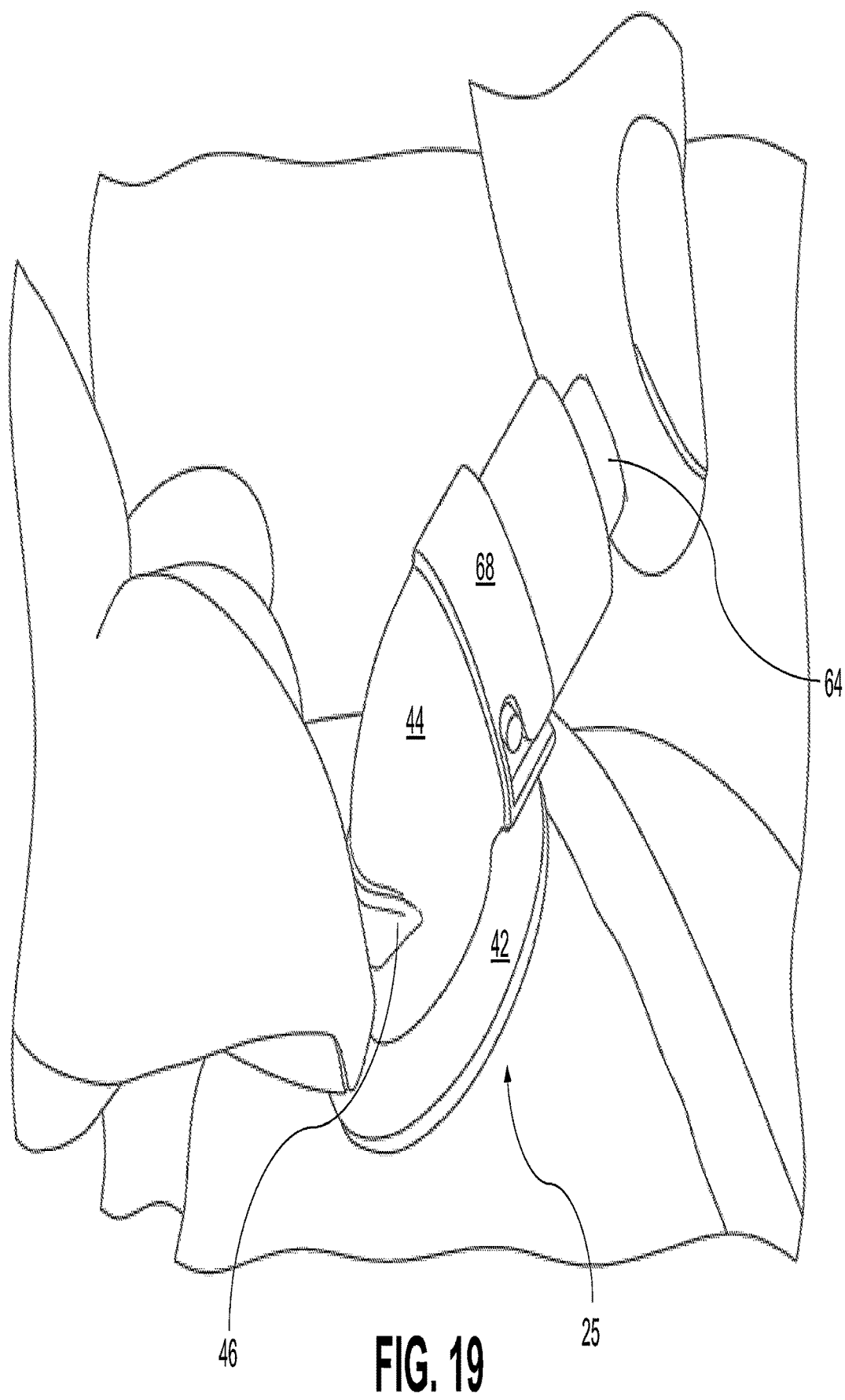
FIG. 19 depicts a user interacting with a system, according to at least some embodiments described herein.

As depicted in FIG. 14-FIG. 19, the second embodiment of the flange 25 includes a body component 44 and a planar portion 42. The body component 44 of the second embodiment of the flange 25 has a first end disposed opposite a second end. The planar portion 42 of the second embodiment of the flange 25 has a first side disposed opposite a second side. The second end of the body component 44 is affixed to the first side of the planar portion 42. The second embodiment of the flange 25 comprises an opening disposed therein. The second end of the body component 44 comprises a lip portion 46. The lip portion 46 of the body component 44 is configured to be grasped by a user when utilizing the system. It should be appreciated that the lip portion 46 is present in some embodiments and such depiction and representation is not indicative of all representations. For example, the body component 44 may include other shapes and/or styles. Specifically, a user's index finger may be placed on the lip portion 46 of the body component of the flange component 42, while the users thumb is placed on the first end 64 of the plunger component 36, as shown in FIG. 19. It should be appreciated that this example is provided for illustrative purposes only and other uses are acceptable. Moreover, as shown in FIG. 16, the second side of the planar portion 42 comprises a bore opening 74 with rounded edges to keep the output from the ostomy collection pouch 20 from clogging the hole/opening.

Figure 17:
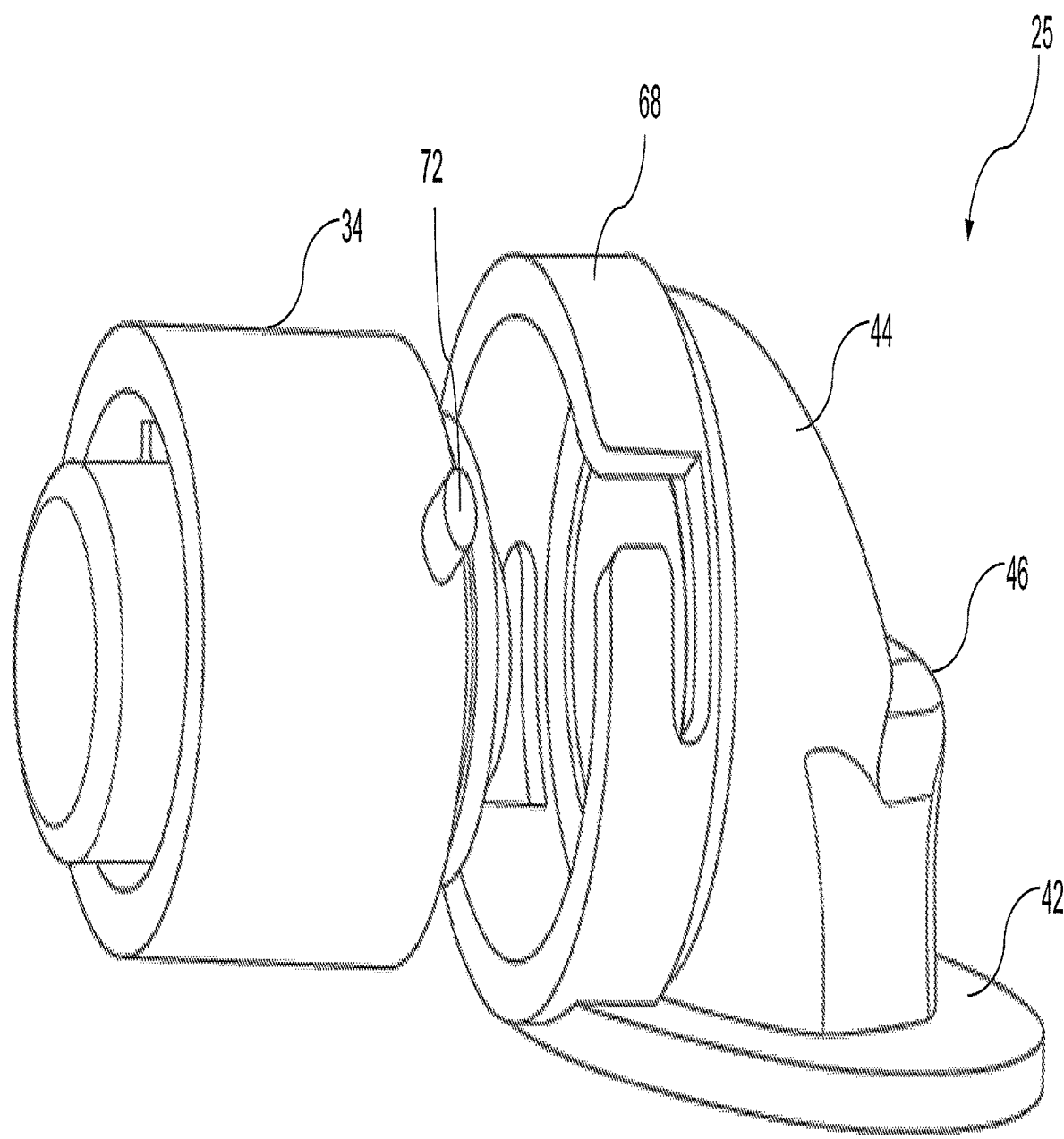
FIG. 17 depicts a front perspective view of a valve body and a second embodiment of a flange, according to at least some embodiments described herein.
Figure 18:
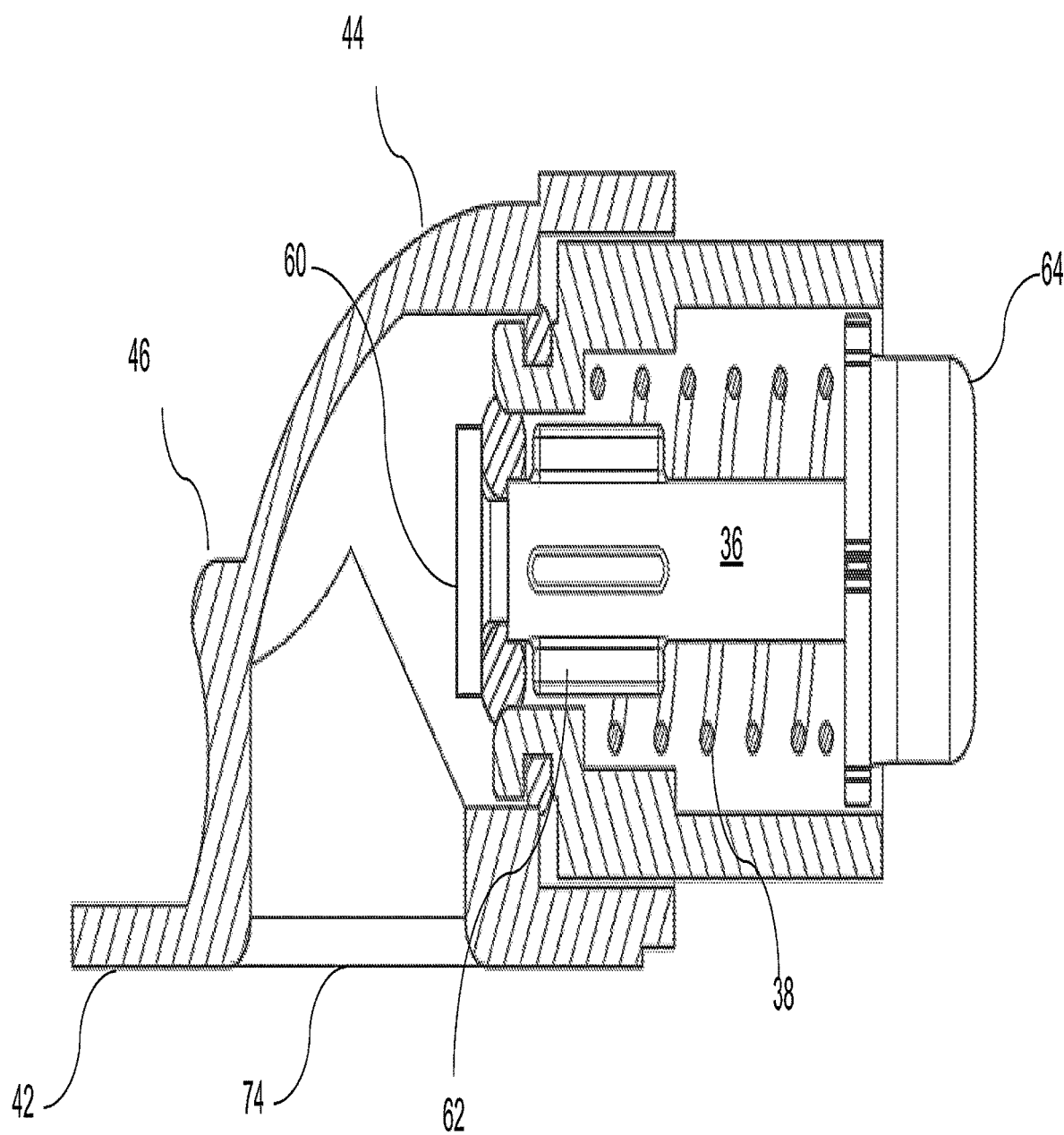
FIG. 18 depicts a cutaway view of components of a system, according to at least some embodiments described herein.

As shown in FIG. 15 and FIG. 17, the first end of the second embodiment of the flange comprises a first opening 70 in the collar 68 parallel to the planar portion 42. The first opening 70 is affixed perpendicular to a second opening 76 of the collar 68. In response to the second embodiment of the flange 25 receiving the valve assembly therein, the first opening 70 is configured to receive the at least one protrusion 72 of the body component of the valve body 34. The valve assembly is rotated such that the at least one protrusion 72 of the body component of the valve body 34, the valve body having a terminal end 66, moves from the first opening 70 to the second opening 76 to lock the valve assembly to the second embodiment of the flange 25.

As explained, the second embodiment of the flange 25 is affixed to a hole in a wall of the ostomy collection pouch 20. Moreover, once the second embodiment of the flange 25 receives the valve assembly therein, a force may be exerted on the first end 64 of the plunger component 36 to permit gaseous communication from an interior to an exterior of the ostomy collection pouch 20. Upon release of the force exerted on the first end 64 of the plunger component 36, the gaseous communication is prevented between the interior and the exterior of the ostomy collection pouch 20. The one or more protrusions (or fins or wings) 62 of the plunger component 36 ensures that the plunger component 36 remains centered in the valve body 34 and ensure a proper seal occurs when the valve closes. Moreover, during these actions, the spring 38 acts against the valve body 34 to allow for an action on the plunger component 36. It should be appreciated that this example could utilize a manual filter.

As described herein, the components of the system may comprise any bio-safe material. In some examples, the components of the system may comprise a silicone material. However, the material comprising these components is not limited to the materials described herein and other materials are contemplated.

When introducing elements of the present disclosure or the embodiments thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A system for use in venting a gas from an interior of an ostomy collection pouch, the system comprising:
    a valve assembly, the valve assembly comprising:
        a plunger component;
        a spring component;
        a valve body having at least one protrusion;
        a first sealing component; and
        a second sealing component; and
    a flange component affixed to a hole in a wall of the ostomy collection pouch,
        wherein the flange component has at least one channel configured to receive the at least one protrusion of the valve body,
        wherein the flange component is curved such that the valve assembly, when engaged with the flange component, is substantially parallel to a planar portion of the flange component,
        wherein the flange component is configured to receive the valve assembly therein such that responsive to a force exerted on a first end of the plunger component, gaseous communication is permitted from an interior to an exterior of the ostomy collection pouch, and upon release of the force exerted on the first end of the plunger component, the gaseous communication is prevented between the interior and the exterior of the ostomy collection pouch, and
        wherein a second side of a body component of the flange component comprises a lip portion.

2. The system of claim 1, wherein the plunger component comprises:
    the first end disposed opposite a second end; and
    a body component disposed between the first end and the second end,
        wherein the body component comprises one or more protrusions extending from the body component proximate the second end, and
        wherein a width of the body component is smaller than a width of the first end and a width of the second end.

3. The system of claim 2, wherein the body component of the plunger component is received by the spring component.

4. The system of claim 3, wherein the plunger component and the spring component are received by the valve body.

5. The system of claim 1, wherein the valve body comprises:
    a first end of the valve body disposed opposite a second end of the valve body;
    a body component disposed between the first end of the valve body and the second end of the valve body; and
    a recessed portion affixed between the second end of the valve body and a ring component.

6. The system of claim 5, wherein the recessed portion is configured to receive the first sealing component.

7. The system of claim 5, wherein the second sealing component is received by the second end of the body portion of the valve body.

8. The system of claim 1, wherein
    the body component of the flange component has a first end disposed opposite a second end; and
    the planar portion having a first side disposed opposite the second side,
        wherein the second end of the body component of the flange component is affixed to the first side of the planar portion.

9. The system of claim 8, wherein the lip portion of the body component of the flange component is configured to be grasped by a user when utilizing the system.

10. The system of claim 8,
    wherein the first end of the flange component comprises a first opening parallel to the planar portion of the flange component, and
    wherein the first opening of the flange component is affixed perpendicular to a second opening.

11. The system of claim 10, wherein, in response to the flange component receiving the valve assembly therein, the first opening is configured to receive the at least one protrusion of the valve body.

12. The system of claim 11, wherein the valve assembly is configured to rotate such that the at least one protrusion of the valve body moves from the first opening to the second opening to lock the valve assembly to the flange component.

13. The system of claim 1, wherein a first circumference of the first sealing component is larger than a second circumference of the second sealing component.

14. The system of claim 1, further comprising:
    a filter affixed on an interior surface of a wall of the ostomy collection pouch over a hole or on an outside of the ostomy collection pouch between the ostomy collection pouch and the flange component.

15. The system of claim 14, wherein the filter is selected from the group consisting of: a charcoal filter, a hydrophobic filter, and a hydrophilic filter.

16. The system of claim 1, wherein one or more components of the system comprise a bio-safe material, and wherein the valve assembly is removable and/or reusable in another medical device.

17. The system of claim 1, wherein each of the first sealing component and the second sealing component comprise O-rings.

18. The system of claim 1, wherein the first sealing component seals the valve body to the flange component.

19. The system of claim 1, wherein the second sealing component seals the valve body and seals the plunger component to the valve body.

20. The system of claim 1, wherein rotation of the valve assembly from a first position to a second position causes the at least one protrusion to engage the at least one channel thereby locking the valve assembly to the flange component.

* * * * *